US00PP13068P2

(12) United States Plant Patent
Wain

(10) Patent No.: US PP13,068 P2
(45) Date of Patent: Oct. 8, 2002

(54) CHRYSANTHEMUM PLANT NAMED 'CEDAR FALLS'

(75) Inventor: Peter Wain, Locksheath (GB)

(73) Assignee: Fides Goldstock Breeding B.V., Maasland (NL)

( * ) Notice: Subject to any disclaimer, the term of this patent is extended or adjusted under 35 U.S.C. 154(b) by 0 days.

(21) Appl. No.: 09/996,393

(22) Filed: Nov. 30, 2001

(51) Int. Cl.[7] ..... A01H 5/00

(52) U.S. Cl. ..... Plt./286

(58) Field of Search ..... Plt./286

*Primary Examiner*—Bruce R. Campell
*Assistant Examiner*—Anne Marie Grünberg
(74) *Attorney, Agent, or Firm*—C. A. Whealy

(57) ABSTRACT

A distinct cultivar of Chrysanthemum plant named 'Cedar Falls', characterized by its uniform and upright plant habit; strong and freely branching growth habit; dark green foliage; uniform flowering habit; eight-week response time; large daisy-type inflorescences; red and yellow bi-colored ray florets; and good postproduction longevity.

1 Drawing Sheet

BOTANICAL CLASSIFICATION/CULTIVAR DENOMINATION

*Chrysanthemum×morifolium* cultivar Cedar Falls.

BACKGROUND OF THE INVENTION

The present Invention relates to a new and distinct cultivar of Chrysanthemum plant, botanically known as *Chrysanthemum×morifolium* and hereinafter referred to by the name 'Cedar Falls'.

The new Chrysanthemum is a product of a planned breeding program conducted by the Inventor in Fareham, Hampshire, United Kingdom. The objective of the breeding program is to create new potted Chrysanthemum cultivars with uniform plant growth habit, desirable inflorescence form and floret colors, and good postproduction longevity.

The new Chrysanthemum originated from a cross made by the Inventor in February, 1998, in Fareham, Hampshire, United Kingdom, of a proprietary Chrysanthemum seedling selection identified as code number 201w 1, not patented, as the female, or seed, parent with a proprietary Chrysanthemum seedling selection identified as code number 96w 24, not patented, as the male, or pollen, parent. The new Chrysanthemum was discovered and selected by the Inventor as a single flowering plant within the progeny of the stated cross grown in a controlled environment in Fareham, Hampshire, United Kingdom. The selection of this plant was based on its desirable infloresence form and red and yellow bi-colored ray florets.

Asexual reproduction of the new Chrysanthemum by vegetative tip cuttings was first conducted in Fareham, Hampshire, United Kingdom in February, 1999. Asexual reproduction by vegetative tip cuttings has shown that the unique features of this new Chrysanthemum are stable and reproduced true to type in successive generations.

SUMMARY OF THE INVENTION

The cultivar Cedar Falls has not been observed under all possible environmental conditions. The phenotype may vary somewhat with variations in environment such as temperature, daylength, and/or light level, without, however, any variance in genotype.

The following traits have been repeatedly observed and are determined to be the unique characteristics of 'Cedar Falls'. These characteristics in combinatioin distinguish 'Cedar Falls' as a new and distinct Chrysanthemum:

1. Uniform and upright plant habit.
2. Strong and freely branching growth habit.
3. Dark green foliage.
4. Uniform flowering habit.
5. Can be grown as a disbud or spray-type.
6. Eight-week response time.
7. Large daisy-type inflorescences that are about 9.1 cm in diameter.
8. Red and yellow bi-colored ray florets.
9. Good postproduction longevity with plants maintaining good substance and color for about three weeks in an interior environment.

Plants of the new Chrysanthemum differ primarily from plants of the female parent selection in ray floret coloration as plants of the new Chrysanthemum have red and yellow bi-colored ray florets whereas plants of the female parent selection have purple-colored ray florets. In addition, plants of the new Chrysanthemum have larger inflorescences than plants of the female parent selection.

Plants of the new Chrysanthemum are similar to plants of the male parent selection in ray floret coloration, however plants of the new Chrysanthemum are shorter and flower later than plants of the male parent selection.

Plants of the new Chrysanthemum can be compared to plants of the cultivar Yoauburn, disclosed in U.S. Plant Pat. No. 12,526. In side-by-side comparisons conducted by the Inventor in Fareham, Hampshire, United Kingdom, plants of the new Chrysanthemum differed from plants of the cultivar Yoauburn in the following characteristics:

1. Plants of the new Chrysanthemum had larger inflorescences than plants of the cultivar Yoauburn.
2. Plants of the new Chrysanthemum flowered about 10 days later than plants of the cultivar Yoauburn.
3. Plants of the new Chrysanthemum and the cultivar Yoauburn differed in ray floret coloration as plants of the new Chrysanthemum had red and yellow bi-colored ray florets whereas plants of the cultivar Yoauburn had bronze-colored ray florets.

Plants of the new Chrysanthemum can also be compared to plants of the cultivar Kenya, not patented. In side-by-side comparisons conducted by the Inventor in Fareham, Hampshire, United Kingdom, plants of the new Chrysanthemum differed from plants of the cultivar Kenya in the following characteristics:

1. Plants of the new Chrysanthemum flowered about 7 days later than plants of the cultivar Kenya.

2. Plants of the new Chrysanthemum and the cultivar Kenya differed in ray floret coloration as plants of the new Chrysanthemum had red and yellow bi-colored ray florets whereas plants of the cultivar Kenya had solid red-colored ray florets.

BRIEF DESCRIPTION OF THE PHOTOGRAPHS

The accompanying colored photographs illustrate the overall appearance of the new Chrysanthemum showing the colors as true as it is reasonably possible to obtain in colored reproductions of this type. Colors in the photographs may differ from the color values cited in the detailed botanical description which accurately describe the colors of the new Chrysanthemum.

The photograph at the top of the first sheet comprises a side perspective view of a typical flowering plant of 'Cedar Falls' grown as a disbud-type.

The photograph at the bottom of the sheet comprises a close-up view of typical inflorescences of 'Cedar Falls' grown as a disbud-type.

DETAILED BOTANICAL DESCRIPTION

In the following description, color references are made to The Royal Horticultural Society Colour Chart, version 1995, except where general terms of ordinary dictionary significance are used. The aforementioned photographs and following observations and measurements describe plants grown and flowered during the summer and autumn in Leamington, Ontario, Canada, in a fiberglass-covered greenhouse and under conditions which approximate those generally used in commercial potted Chrysanthemum production. Four unrooted cuttings were directly stuck in 15-cm containers, exposed to long day/short night conditions, and pinched once about 14 days later. At the time of pinching, the photoinductive short day/long night treatments were started. Plants used for this description were grown as disbud-types. Measurements and numerical values represent averages of typical flowering plants.

Botanical classification: *Chrysanthemum×morifolium* cultivar Cedar Falls.

Commercial classification: Daisy-type potted Chrysanthemum.

Parentage:

*Female, or seed, parent.*—Proprietary *Chrysanthemum×morifolium* seedling selection identified as code number 201w 1, not patented.

*Male, or pollen, parent.*—Proprietary *Chrysanthemum×morifolium* seedling selection identified as code number 96w 24, not patented.

Propagation:

*Type.*—Vegetative tip cuttings.

*Time to initiate roots.*—About four days at 21° C.

*Time to produce a rooted cutting.*—About ten days at 21° C.

*Root description.*—White, fibrous.

*Rooting habit.*—Freely branching.

Plant description:

*Appearance.*—Herbaceous daisy-type potted Chrysanthemum that can be grown as a disbud or as a spray-type. Stems mostly upright; uniform crown. Freely branching, about four lateral branches develop after removal of teminal apex (pinching); dense and full plants.

*Plant height.*—About 31.5 cm.

*Plant diameter or spread.*—About 35 cm.

*Lateral branches (peduncles).*—Length: About 27 cm. Diameter: About 5 mm. Internode length: About 1.7 cm. Strength: Strong. Texture: Pubescent. Color: 144A to 146A.

*Foliage description.*—Arrangement: Alternate. Length: About 5.5 cm. Width: About 4.2 cm. Apex: Cuspidate to mucronate. Base: Attenuate. Margin: Palmately lobed, sinuses between lateral lobes mostly parallel to divergent. Texture: Upper and lower surfaces with very fine pubescence; veins prominent on lower surface. Color: Young and fully expanded foliage, upper surface: Slightly darker than 147A. Young and fully expanded foliage, lower surface: Slightly darker than 147B. Venation, upper and lower surfaces: 147B. Petiole length: About 9 mm. Petiole diameter: About 3 mm. Petiole color: Upper surface: Close to 147B. Lower surface: Close to 147C.

Inflorescence description:

*Appearance.*—Daisy-type inflorescence form with elongated oblong-shaped ray florets. Inflorescences borne on terminals above foliage. Disk and ray florets arranged acropetally on a capitulum. Not fragrant. Can be grown as a disbud or spray-type. Flowering response: Under natural conditions, plants flower in the autumn/winter in the Northern Hemisphere. At other times of the year, inflorescence initiation and development can be induced under short day/long night conditions (at least 13.5 hours of darkness). Early flowering; plants exposed to two weeks of long day/short night conditions followed by photoinductive short day/long night conditions flower about 8 weeks later.

*Postproduction longevity.*—Inflorescences maintain good color and substance for about three weeks in an interior environment.

*Quantity of inflorescences.*—Grown as a disbud-type, only one inflorescence, the terminal inflorescence, develops per lateral branch.

*Inflorescence bud.*—Height: About 6 mm. Diameter: About 8 mm. Color: Darker than 143A.

*Inflorescence size: Diameter: about* 9.1 cm. Depth (height): About 1.8 cm. Diameter of disc: About 2.4 cm. Receptacle diameter: About 7.5 mm.

*Ray florets.*—Shape: Elongated-oblong. Orientation: Initially upright, then about 90° from vertical. Aspect: Flat to slightly convex. Length: About 4.2 cm. Width: About 9 mm. Apex: Acute or emarginate. Base: Attenuate; short corolla tube. Corolla tube length: About 5 mm. Margin: Entire. Texture: Smooth, velvety. Number of ray florets per inflorescence: About 32 arranged in one or two rows. Color: When opening and fully expanded, upper surface: Towards apex, yellow, 9A; mid-section and base, yellow, 9A, overlain with red, 45A to 46A. With subsequent development, ray florets become more yellow with less red. When opening and fully expanded, lower surface: Towards apex, yellow, 9A to 9B; mid-section and base, yellow, 9A to 9B, underlain with red, 46A to 53A.

*Disc florets.*—Arrangement: Massed at center of receptacle. Shape: Tubular, elongated. Apex: Five-pointed. Length: About 6.5 mm. Width: Apex: About 1.7 mm. Base: About 1 mm. Number of disc florets per inflorescence: About 285. Color: Immature: 144A to 154A. Mature: Apex: 9A. Mid-section and base: Closest to 155D.

*Phyllaries.*—Quantity per inflorescence: About 24. Length: About 8 mm. Width, at base: About 3 mm. Shape: Elongated, linear. Apex: Acute. Base: Truncate. Texture: Upper surface, smooth; lower surface, pubescent. Color, upper and lower surfaces: 147A.

*Reproductive organs.*—Androecium: Present on disc florets only. Anther color: 9A. Pollen amount: Scarce. Pollen color: 15A. Gynoecium: Present on both ray and disc florets.

*Seed.*—Seed production has not been observed.

Disease resistance: Resistance to pathogens common to Chrysanthemums has not been observed on plants grown under commercial greenhouse conditions.

It is claimed:

1. A new and distinct cultivar of Chrysanthemum plant named 'Cedar Falls', as illustrated and described.

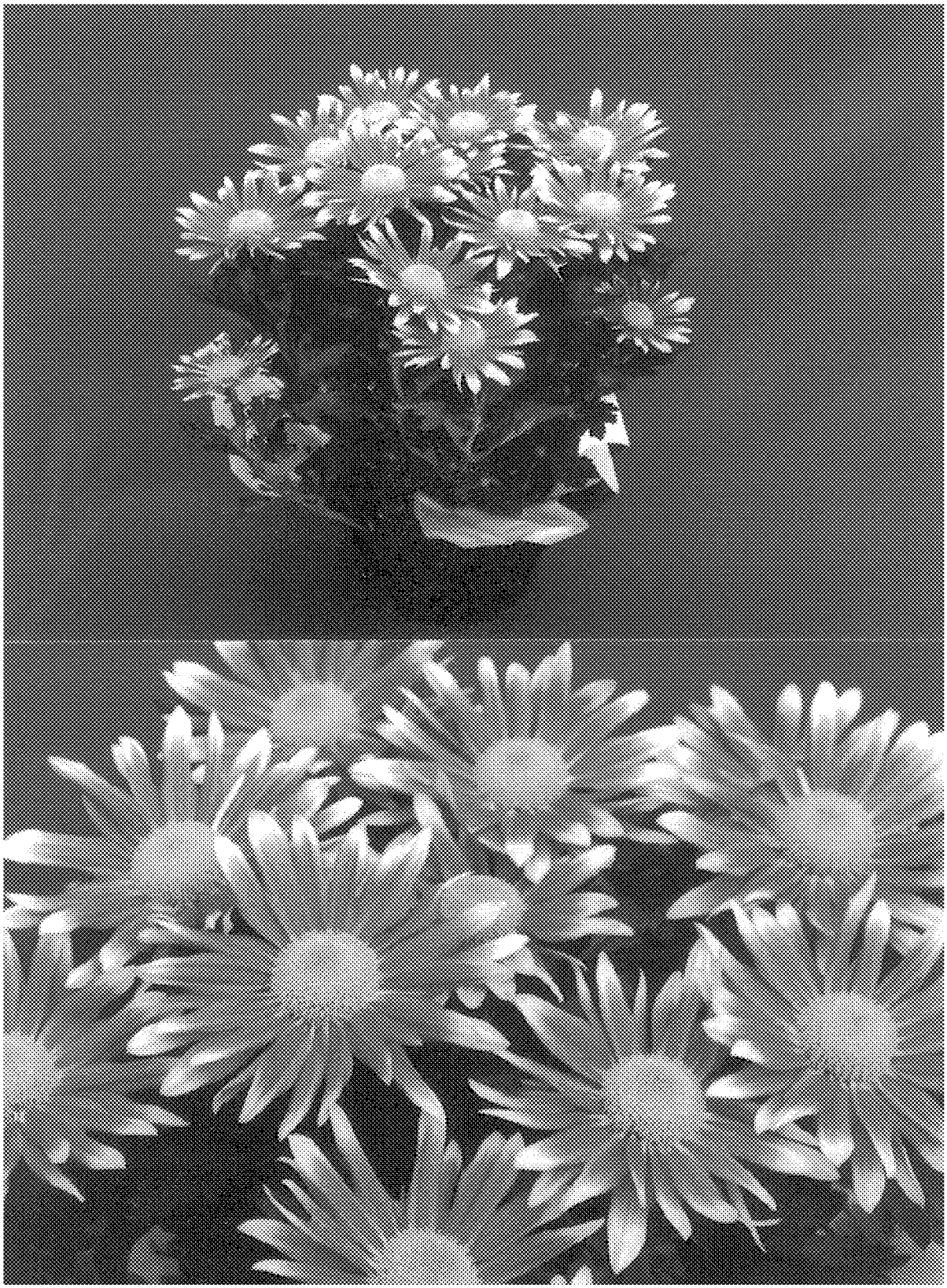

* * * * *